United States Patent [19]

Jones et al.

[11] Patent Number: 5,686,614
[45] Date of Patent: Nov. 11, 1997

[54] PREPARATION OF CHIRAL 5-AMINOCARBONYL-5H-DIBENZO[A,D]CYCLOHEPTEN-5,10-IMINES BY OPTICAL RESOLUTION

[75] Inventors: Tappey H. Jones, Lexington, Va.; Kenner C. Rice, Bethesda, Md.

[73] Assignee: Neurogen Corporation, Branford, Conn.

[21] Appl. No.: 420,013

[22] Filed: Apr. 11, 1995

[51] Int. Cl.[6] .................................................. C07D 471/08
[52] U.S. Cl. .................................................. 546/43; 546/72
[58] Field of Search .................................................. 546/43, 72

[56] References Cited

U.S. PATENT DOCUMENTS

| | | | |
|---|---|---|---|
| 4,399,141 | 8/1983 | Anderson et al. | 424/256 |
| 4,477,668 | 10/1984 | Bender et al. | 546/72 |
| 5,196,415 | 3/1993 | Monn et al. | 514/210 |

FOREIGN PATENT DOCUMENTS

| | | |
|---|---|---|
| 2004872 | 4/1979 | United Kingdom . |
| 2 061 947 A | 5/1981 | United Kingdom . |

OTHER PUBLICATIONS

Rogawski, et al., (1991), "Anticonvulsant Activity of Low–Affinity Uncompetitive N–Methyl–D–aspartate Antagonist (±)–5–Aminocarbonyl–10,11–dihydro–5H–dibenzo[a,d]cyclohepten–5,10–imine(ADCI): Comparison with the Structural Analogs Dizocilpine (MK–801) and Carbamazepine," *J. Pharmacology and Experimental Therapeutics*, vol. 259, No. 1, pp. 30–37.

Grant, et al., (1991), *J. Pharmacology and Experimental Therapeutics*, vol. 260, No. 3, pp. 1017–1022.

*Primary Examiner*—Philip I. Datlow
*Attorney, Agent, or Firm*—McDonnell Boehnen Hulbert & Berghoff

[57] ABSTRACT

Disclosed are processes for resolving a racemic mixture of 5-aminocarbonyl-5H-dibenzo[a,d]cyclohepten-5,10-imines into component enantiomers comprising recrystallizaton of diasteriomeric tartrate salts.

12 Claims, No Drawings

PREPARATION OF CHIRAL 5-AMINOCARBONYL-5H-DIBENZO[A,D]CYCLOHEPTEN-5,10-IMINES BY OPTICAL RESOLUTION

STATEMENT OF GOVERNMENT INTEREST

This invention was made pursuant to a Cooperative Research and Development Agreement between Neurogen Corporation and the National Institutes of Health, United States of America. The government has certain rights in the invention.

BACKGROUND OF THE INVENTION

1. Field of the Invention

This invention relates to the field of pharmaceutical chemistry, and provides an advantageous process for resolving racemic mixtures of 5-aminocarbonyl-5H-dibenzo[a,d]cyclohepten-5,10-imines. More specifically, the present application relates to the optical resolution of enantiomers, i.e., chiral antipodes, of 5-aminocarbonyl-5H-dibenzo[a,d]cyclohepten-5,10-imines by recrystallizing a mixture of salts of the amines.

2. Description of the Related Art

U.S. Pat. No. 5,196,415 discloses various 5-aminocarbonyl-5H-dibenzo[a,d]cyclohepten-5,10-imines and methods for preparing such compounds. The methods disclosed there involve conversion of C5-unsubstituted-10,11-dihydro-5H-dibenzo[a,d]cyclohepten-5,10-imines into their N-tert-butylformamidine derivatives followed by formation of the C5-substituted ethyl ester. After removal of the tert-butylformamidine moiety from the nitrogen atom of the ring system, the ester functionality is replaced with an amide group by warming the ester in methanol with the appropriate amine derivative. If N-substitution is desired, the secondary amine is allowed to react with the appropriate alkyl halide in the presence of a suitable base. When the initial reaction employs a racemic mixture of C5-unsubstituted-10,11-dihydro-5H-dibenzo[a,d]cyclohepten-5,10-imines, the resulting product is a racemic mixture of 5-aminocarbonyl-5H-dibenzo[a,d]cyclohepten-5,10-imines.

Racemic mixtures of 5-aminocarbonyl-5H-dibenzo[a,d]cyclohepten-5,10-imines are known to have pharmacological activity as anticonvulsant agents. See, for example, Rogawski et at., 1991, *J. Pharmacology and Experimental Therapeutics*, 259: 30–37; and Grant et al., 1992, *J. Pharmacology and Experimental Therapeutics*, 260: 1017–1022.

The separation of diastereomers by chromatographic methods is well known. However, unlike diastereomers, enantiomers (optical antipodes of chiral compounds) are not separable by standard chromatographic methods; pure enantiomers must be prepared either by lengthy chiral syntheses or through optical resolution.

Optical resolution is empirical and highly specific to the enantiomers to be separated. It is well recognized that salt formation and solubility parameters are very critical to obtaining a system for achieving resolution of enantiomers from a racemic mixture. Much experimentation is necessary to find the proper combination for each individual resolution. Among the most difficult enantiomers to resolve are those wherein the molecule possesses a high degree of spacial symmetry about the chiral centers.

Such a situation is found in the case of dibenzo[a,d]cyclohepten-5,10-imines where the structural features about the central amine nitrogen are virtually identical for the two enantiomers as shown in Scheme 1 below. In the case of the 5-aminocarbonyl-5H-dibenzo[a,d]cyclohepten-5,10-imines such as those described in U.S. Pat. No. 5,196,415, the R group in Scheme 1 represents a primary amide functionality.

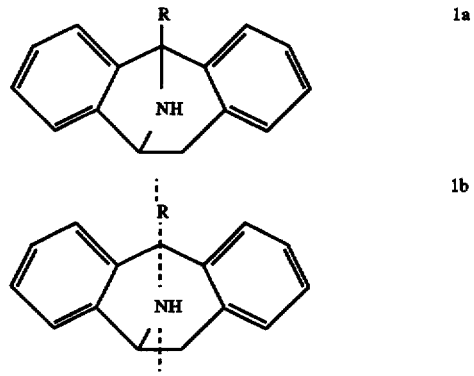

Scheme 1

In Scheme 1, Formula 1a is a 5-substituted-5H-dibenzo[a,d]cyclohepten-5,10 imine and Formula 1b shows the line of of symmetry.

Although the general class of 5-substituted-5H-dibenzo[a,d]cyclohepten-5,10 imines of structure 1 a above was first described over 20 years ago, there has been described only one method of carrying out an optical resolution for 5-dibenzo[a,d]cyclohepten-5,10-imines. British patent application GB 2 004 872 (Anderson et al.) describes the optical resolution of 5-methyl-10,11-dihydro-5H-dibenzo[a,d]cyclohepten-5,10-imine. The methods described in British patent application GB 2 004 872 require an acid and a solvent that are substantially different from the materials used in the present method. Moreover, the compounds in the racemic mixtures resolved by the procedures outlined in that patent are much simpler than structure 5-aminocarbonyl-5H-dibenzo[a,d]cyclohepten-5,10-imine. In fact, the methods described in that patent are not capable of resolving racemic mixtures of 5-aminocarbonyl-5H-dibenzo[a,d]cyclohepten-5,10-imine.

SUMMARY OF THE INVENTION

The present invention provides a method for resolving racemic mixtures of 5-aminocarbonyl-5H-dibenzo[a,d]cyclohepten-5,10-imines of Formula 2. Such racemic mixtures can be prepared by the method described in U.S. Pat. No. 5,196,415.

Thus the invention provides methods for preparing chiral compounds of Formula 2. The inventive methods involve optical resolution of racemic mixtures of 5-aminocarbonyl-5H-dibenzo[a,d]cyclohepten-5,10-imines, i.e., compounds of Formula 2:

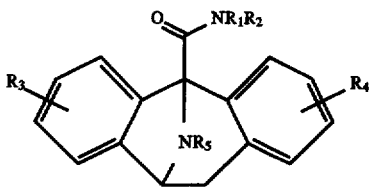

wherein each of $R_1$ and $R_2$ is independently selected from hydrogen, linear or branched alkyl groups of from one to about twenty carbon atoms, alkenyl groups from two to about twenty carbon atoms, alkynyl groups from two to about twenty carbon atoms, cycloalkyl groups of three to about eight carbon atoms, cycloalkenyl groups of from three to about eight carbon atoms, and wherein $R_1$ and $R_2$ may be taken together to form a N-containing cyclic structure having two to about eight carbon atoms, any of the said groups being optionally substituted with one or more substituents selected from alkyl, haloalkyl, hydroxyalkyl, alkenyl, oxo, hydroxyl, alkoxy, thio, alkoxyalkyl, amino, halo, cyano, or mercapto, and wherein $R_3$ and $R_4$ are independently selected from hydrogen, linear or branched alkyl groups of from one to about ten carbon atoms, alkenyl groups from two to about ten carbon atoms, alkynyl groups from two to about ten carbon atoms, hydroxyl, amino, alkylamino, alkoxy, cyano, nitro, haloalkyl, and mercapto, and wherein $R_5$ is selected from hydrogen, linear or branched alkyl groups of from one to about ten carbon atoms, alkenyl groups from two to about ten carbon atoms, alkynyl groups from two to about ten carbon atoms, hydroxyl, phenyl, haloalkyl, aminoalkyl, 1-phenylmethyl, 2-phenylmethyl, and alkoxy, and wherein $R_1$ and $R_5$ taken together may form a cyclic structure containing two nitrogen atoms possessing from two to about six carbon atoms, any of the said groups being optionally substituted by alkyl, oxo, thio, alkoxy, hydroxy, amino, alkylamino, phenyl, haloalkyl and thio.

The invention involves first forming a mixture of diasteriomeric salts of the amines followed by subsequent recrystallization of the solid mixture to yield a product containing one enantiomer in an enantiomeric excess. The mixture of salts is recrystallized from an ethanol/water solvent system. Such a solvent is capable of dissolving both enantiomers at a first temperature but only one enantiomer at a second, lower temperature.

The invention also involves first forming a mixture of tartrate salts of the amines followed by subsequent recrystallization of the mixture to yield a product containing a certain enantiomer in an enantiomeric excess. The mixture of tartrate salts is dissolved in a solvent system capable of dissolving both enantiomers at a first temperature but only one enantiomer at a second, lower temperature.

DETAILED DESCRIPTION OF THE INVENTION

In this document, all temperatures will be stated in degrees Celsius. All amounts, ratios, concentrations, proportions and the like will be stated in weight units, unless otherwise stated, except for ratios of solvents, which are in volume units.

Where the term 'alkyl' is used, either alone or within other terms such as 'haloalkyl' or 'alkylamino' the term 'alkyl' embraces linear or branched radicals having one to about ten carbon atoms. Preferred alkyl radicals are "lower alkyl" radicals having from one to about five carbon atoms. The term 'cycloalkyl' embraces radicals having from three to about ten carbon atoms, such as cyclopropyl and cyclobutyl. The term "haloalkyl" embraces radicals wherein one or more of the alkyl carbon atoms is substituted with one or more halogens atoms, preferably selected from fluoro, chloro and bromo. Specifically embraced by the term 'haloalkyl' are monohaloalkyl, dihaloalkyl and polyhaloalkyl groups. Examples of a polyhaloalkyl are trifluoromethyl, 2,2,2-trifluoroethyl and perfluoroethyl. The term 'alkenyl' embraces linear or branched radicals having from two to about ten carbon atoms and containing at least one double bond. The term 'alkynyl' embraces linear or branched radicals having from two to about ten carbon atoms containing at least one carbon-carbon triple bond. The term 'alkoxy' embraces linear or branched oxy-containing radicals having alkyl portions of from one to about ten carbon atoms, such as methoxy group. The alkoxy radicals may be further substituted with one or more halo atoms, such as fluoro, chloro or bromo to provide haloalkoxy groups. The term 'alkylamino' embraces linear or branched nitrogen containing radicals where the nitrogen atom may be substituted with from one to three alkyl radicals of from one to about ten carbon atoms, such as N-methylamino and N,N-dimethylamino.

Specific examples of alkyl groups are methyl, ethyl, propyl, isopropyl, n-butyl, isobutyl, tert-butyl, sec-butyl, neopentyl and n-pentyl. Typical alkenyl groups may have one unsaturated double bond, such as allyl or may have a plurality of double bonds.

By "enantiomeric excess" as used herein is meant more of one enantiomer than the other enantiomer.

By "racemic mixture" as used herein is meant a 50:50 by weight mixture of two enantiomers.

By "optical resolution" or "resolution" as used herein is meant a process of separating a racemic mixture into the two component enantiomers or optical isomers.

The following group of representative products of the process and of this invention will be mentioned, to assure that the reader fully understands the overall purpose of the process:

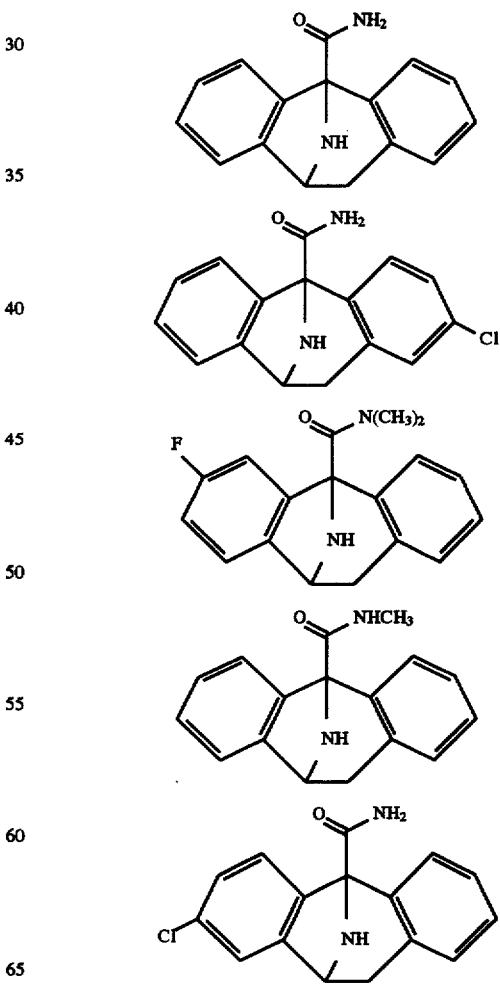

-continued

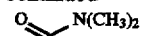
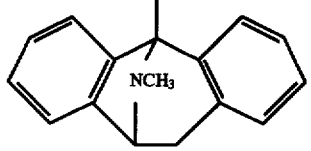

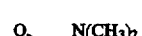
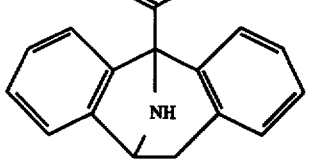

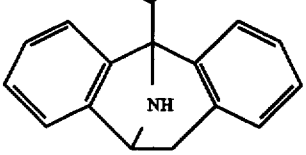

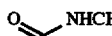
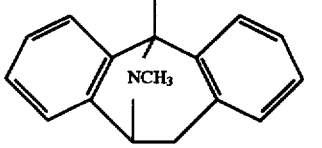

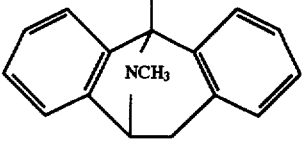

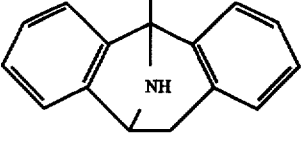

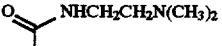
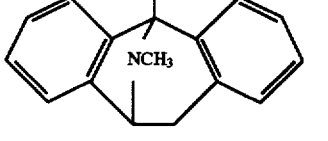

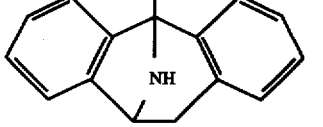

-continued

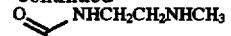
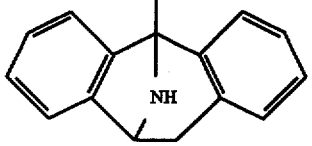

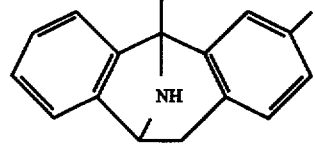

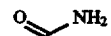
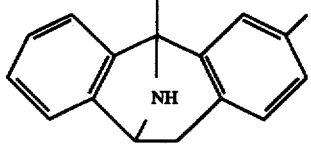

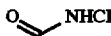
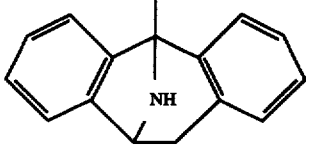

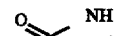
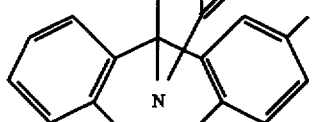

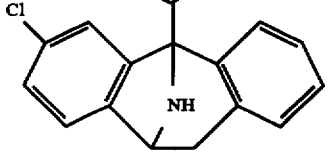

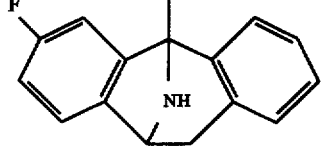

U.S. Pat. No. 5,196,415 teaches that the compounds resolvable by the inventive methods are useful for treatment of patients with generalized epilepsy or partial (symptomatic) epilepsy. These compounds are also useful for treating drug craving in patients addicted to cocaine.

Administration of compounds within Formula 2 to humans can be by any technique capable of introducing the compounds into the bloodstream of a human patient, including oral administration, and by intraveneous, intramuscular and subcutaneous injections.

Compounds indicated by prophylactic therapy will preferably be administered in a daily dose generally in the range of 0.1 mg to 100 mg per kilogram of body weight per day. A more preferred dosage will be in the range of 1.0 to 50 mg per kilogram of body weight. A suitable dose can be administered in suitable sub-doses per day.

The active compound is usually administered in a pharmaceutically acceptable formulation, although in some acute-care situations a compound of Formula 2 may be administered alone. Such formulations may comprise the active compound with one or more pharmaceutically acceptable carriers or diluents. Other therapeutic agents may also be present in the formulation. A pharmaceutically acceptable carrier or diluent provides an appropriate vehicle for delivery of the active compound without undesirable side effects. Delivery of the active compound in such formulations may be by various routes such as oral, nasal, buccal or sublingual, or by parenteral administration such as subcutaneous, intramuscular, intravenous or intradermal routes. Delivery of the active compound may also be through the use of controlled release formulations in subcutaneous implants.

Formulations for oral administration may be in the form of capsules containing the active compound dispersed in a binder such as gelatin or hydroxypropylmethyl cellulose, together with one or more of a lubricant, preservative, surface acting or dispersing agent. Such capsules or tablets may contain controlled release formulation as may be provided in a disposition of active compound in hydroxypropylmethyl cellulose.

Formulations for parental administration may be in the form of aqueous or non-aqueous isotonic sterile injection solutions or suspensions. These solutions or suspensions may be prepared from sterile powders or granules having one or more of the carriers or diluents mentioned for use in the formulations for oral administration.

Racemic mixtures of Formula 2 are resolved using the process outlined in Scheme 2.

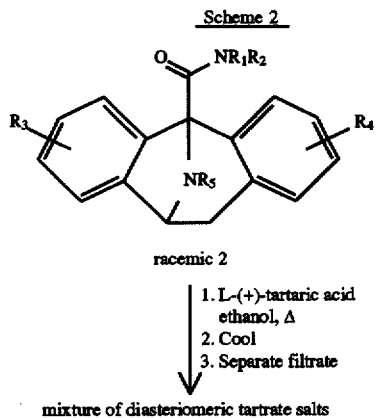

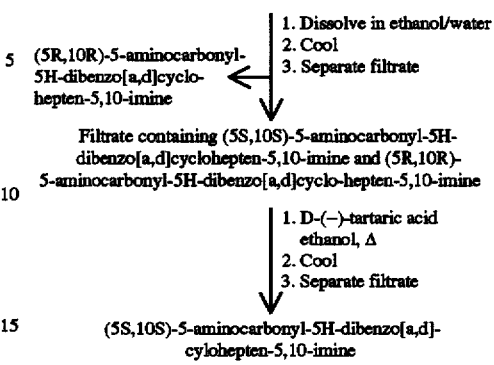

Thus, the invention provides processes for resolving or separating racemic mixtures of 5-aminocarbonyl-5H-dibenzo[a,d]cyclohepten-5,10-imines into their component enantiomers. The process comprises selectively crystallizing a first tartrate salt from a mixture of tartrate salts of the 5-aminocarbonyl-5H-dibenzo[a,d]cyclohepten-5,10-imines. The resolved products contain an enantiomeric excess of either a (5R,10R)-5-aminocarbonyl-5H-dibenzo[a,d]cyclohepten-5,10-imine or a (5S,10S)-5-aminocarbonyl-5H-dibenzo[a,d]cyclo-hepten-5,10-imine.

The (5R,10R)-5-aminocarbonyl-5H-dibenzo[a,d]cyclohepten-5,10-imines (3a) and the (5S,10S)-5-aminocarbonyl-5H-dibenzo[a,d]cyclohepten-5,10-imines (3b) can be represented as follows:

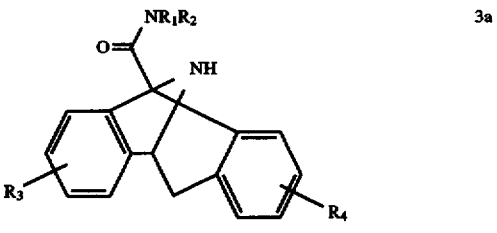

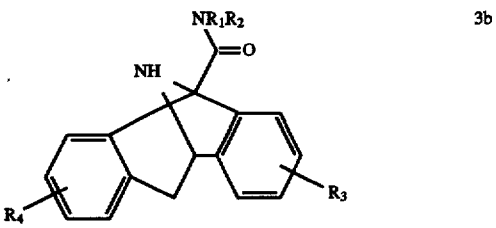

The racemic 5-aminocarbonyl-10,11-dihydro-5H-dibenzo[a,d]cyclohepten-5,10-imine may be prepared according to the procedures set forth in U.S. Pat. No. 5,196,415 from racemic 10,11-dihydro-5H-dibenzo[a,d]cyclohepten-5,10-imine.

The resolution of the racemic material is essentially a recrystallization of diasteriomers of different solubilities from a suitable solvent system. A mixture of diasteriomeric salts (e.g., the (+)-acid salts of a chiral acid) is dissolved in the solvent; upon cooling a single diasteriomer crystallizes. A single enantiomer of the amine is obtained after subsequent neutralizaton of the acid. The filtrate is saved for later resolution of the other enantiomer by recrystallization of the diasteriomer of salt of the (−)-acid.

More specifically, the racemic material is separated into its component enantiomers by first preparing a mixture of diasteriomeric salts by treating the racemic amine mixture with a chiral acid in a suitable solvent, preferably at elevated temperature. The acid is preferably optically pure tartaric, i.e., either D-(−)- or L-(+)-tartaric acid. In preferred embodiments, the tartaric acid is L-(+)-tartaric acid. Representative solvents for this step include mixtures of water and alcohols such as ethanol. Any solids not dissolving in the solvent are removed.

Cooling of the resulting solution affords a mixture of diasteriomeric tartrate salts of either D-(−)- or L-(+)-tartaric acid. The resulting mixture is then dissolved in a solvent capable of dissolving both diasteriomers at elevated temperature but only capable of maintaining one diasteriomer in solution upon cooling. Such a solvent affords a single diasteriomer in an enantiomeric excess. Suitable solvents for accomplishing this separation include mixtures of ethanol and water. Preferred ethanol/water mixtures have volume ratios of ethanol to water of from about 0.1:1 to 10:1. Particularly preferred ethanol/water mixtures have volume ratios of ethanol to water of about 1:1. Upon cooling of the solution of diasteriomeric salts, only one diasteriomer crystallizes, typically in at least 90% enantiomeric excess. The single diasteriomer may be isolated by separating the crystals from the solvent by any suitable means such as, for example, filtration. In preferred embodiments, the diasteriomer isolated first is the salt of L-(+)-tartaric acid. The resulting filtrate, containing the other diasteriomer, is retained for later separation or resolution of the other enantiomer.

The resolved enantiomer may be liberated from the isolated salt of the single diasteriomer by treating the crystalline tartrate salt, preferably the L-(+)-tartrate salt, with a suitable base. Suitable bases are those capable of raising the pH of the solution to a level where 100% by weight of the amine is present as the free amine. Representative bases include various metal hydroxides such as sodium, potassium, and, preferably, ammonium hydroxide. The amount of base is preferably used in molar excess of the acid. The single enantiomer free amine is then isolated by extraction and removal of the solvent. It may subsequently be purified by recrystallization.

Separation or resolution of the other enantiomer from the filtrate containing the other diasteriomer is achieved by first liberating the free base of the amine by treatment with a suitable base followed by extraction and removal of solvent. The resulting free amine is then combined at elevated temperature in a suitable solvent with the opposite enantiomer of the chiral acid used above. I.e., if the acid was L-(+)-tartaric acid in the previous steps, then the acid to be used here is D-(−)-tartaric acid. A preferred acid for the preparation of diasteriomeric salts at this point is D-(−)-tartaric acid.

After cooling the solution, any crystals are separated and redissolved in a solvent capable of dissolving both diasteriomers at elevated temperature but only capable of maintaining one diasteriomer in solution upon cooling. Suitable solvents for accomplishing this step are include mixtures of ethanol and water. Particularly preferred ethanol/water mixtures have volume ratios of ethanol to water of about 1:1. Upon cooling of the solution of diasteriomeric salts, only one diasteriomer crystallizes, typically in at least 90% enantiomeric excess. The crystallized diasteriomer is a salt of the enantiomer resolved above. The single diasteriomer may be isolated by separating the crystals from the solvent by any suitable means such as, for example, filtration.

The resolved second enantiomer may be liberated from the isolated salt of the single diasteriomer by treating the crystalline tartrate salt, preferably the D-(−)-tartrate salt, with a suitable base, as described above. The single enantiomer free amine is then isolated by extraction and removal of the solvent. It may subsequently be purified by recrystallization.

Optical rotations of the resolved materials may be taken using a polarimeter, such as, for example, a Randolph Autopol polarimeter. The absolute configuration of the resolved enantiomers may be determined by single crystal X-ray analysis.

The disclosures in this application of all articles and references, including patents, are incorporated herein by reference.

The invention is illustrated further by the following examples which are not to be construed as limiting the invention in scope or spirit to the specific procedures and compounds described in them.

EXAMPLE 1

Preparation of Racemic 5-aminocarbonyl-10,11-dihydro-5H-dibenzo[a,d]cyclohepten-5,10-imine A mixture of racemic 10,11-dihydro-5H-dibenzo[a,d] cyclohepten-5,10-imine (5.18 g, 25.0 mmol), N'-tert-butyl-N,N-dimethylformamidine (12.84 g, 100.0 mmol) and a few crystals of ammonium sulfate in anhydrous toluene was warmed under reflux for 6 days. Evaporation of the solvent and purification of the crude product by column chromatography employing 7% triethylamine in hexanes as the eluent afforded the N-tert-butylformamidinyl-10,11-dihydro-5H-dibenzo[a,d]cyclohepten-5,10-imine (6.98 g, 24.1 mmol, 96%): mp 63°–64° C.

A solution of this material (5.80 g, 20.0 mmol) in anhydrous ethyl ether (150 mL) under an atmosphere of nitrogen was treated at 5° C. with a 1.25M solution of sec-butyllithium in cylohexane (20.0 mL, 25 mmol). The deep red colored solution of the anion was allowed to stir at this temperature for 40 minutes, then was treated with ethyl chloroformate (2.40 mL, 25.0 mmol). The solution color immediately changed to pale yellow, and gas chromatographic analysis of the reaction mixture demonstrated the complete consumption of the starting material. The reaction mixture was treated with ethanol (100 mL) and $H_2SO_4$ (0.56 mL, 10.0 mmol), and the ether was evaporated under reduced pressure. The ethanolic solution was warmed under reflux for 4 h, then was diluted with 0.5N HCl (100 mL) and extracted with $Et_2O$ (3×100). The aqueous part was made alkaline by addition 1N NaOH, and extracted with $Et_2O$ (3×100). The combined organic part was washed once with $H_2O$ (100 mL), then dried over $K_2CO_3$ and concentrated to dryness affording 5-ethoxycarbonyl-10,11-dihydro-5H-dibenzo[a,d]cyclohepten-5,10-imine (3.37 g, 12.1 mmol, 60%). The hydrogen chloride salt was formed by passing a stream of anhydrous HCl gas through an ethereal solution of the secondary amine: mp 229°–230° C.

A solution of the preceding amino ester (0.53 g, 1.90 mmol) and sodium cyanide (10 mg) in anhydrous methanol (40 mL) which had been previously saturated at 5° C. with ammonia gas was warmed to 60° C. in a sealed tube for 40 h. After cooling to 5° C., the solid which had formed was filtered, washed with $H_2O$, and air-dried affording 5-aminocarbonyl-10,11-dihydro-5H-dibenzo[a,d] cyclohepten-5,10-imine (0.25 g, 1.0 mmol). The filtrate was extracted with $CH_2Cl_2$ (3×50), the organic pool was dried ($K_2CO_3$) and evaporated under reduced pressure, affording an additional quantity of the title compound (0.19 g, 0.76 mmol). Recrystallization of the combined samples from ethanol then gave the analytically pure material (0.37 g, 1.5 mmol, 78%). mp 235°–236° C.

EXAMPLE 2

1. Resolution of (5R,10R)-5-aminocarbonyl-5H-dibenzo[a,d]cyclohepten-5,10-imine A mixture containing 3.0 g (12 mmol) of racemic 5-aminocarbonyl-5H-dibenzo[a,d]cyclohepten-5,10-imine (mp 235°–237° C.) and 1.86 g of L-(+)-tartaric acid in 30 mL of ethanol and 20 mL of water was heated to boiling and the small amounts of solids that did not dissolve were filtered off while the solution was hot. The resulting solution was cooled for 4 hr at ambient temperature and then overnight at −10° C. to provide 2.1 g of L-(+)-tartrate salt. This salt was dissolved in 20 mL of boiling 1:1 ethanol/water solution. After cooling 4 hr at ambient temperature and overnight at −10° C., 1.53 g of crystals were obtained. The filtrate was saved for later use in part 2 of this example. The crystals were treated with an excess of concentrated ammonium hydroxide and the resulting mixture was extracted with methylene chloride. The methylene chloride layer was removed and the residue was recrystallized from 10 mL of 5:1 ethanol/water to provide 0.699 g of (5R,10R)-5-aminocarbonyl-5H-dibenzo[a,d]cyclohepten-5,10-imine, mp=213° C.

2. Resolution of (5S,10S)-5-aminocarbonyl-5H-dibenzo[a,d]cyclohepten-5,10-imine The filtrate saved from part 1 of this example was treated with excess ammonium hydroxide solution and the resulting mixture was subsequently extracted with methylene chloride. Removal of the solvent provided 1.93 g of crude free base. This material was combined with 1.16 g of D-(−)-tartaric acid in 35 mL of boiling 1:1 ethanol/water. The mixture was cooled for 4 hr at ambient temperature and then overnight at −10° C. to provide 1.75 g of crystals. The crystals were then taken up in 35 mL of hot 1:1 ethanol/water and cooled to provide 1.31 g of crystals. The crystals were treated with excess ammonium hydroxide solution and extracted with methylene chloride. After the solvent was removed, the residue was recrystallized from 5:1 ethanol/water to provide 0.724 g of (5S,10S)-5-aminocarbonyl-5H-dibenzo[a,d]cyclohepten-5,10-imine, mp 213° C.

3. Preparation of Isocyanate Derivatives of 5-aminocarbonyl-5H-dibenzo[a,d]cyclohepten-5,10-imine The S-(+)-naphthylethylisocyanate derivative of (5S,10S)-5-aminocarbonyl-5H-dibenzo[a,d]-cyclohepten-5,10-imine was prepared by mixing equal molar amounts of the resolved amine prepared in part 1 above and S-(+)-naphthylethylisocyanate (94% enantiomeric excess) in methylene chloride and concentrating. $^1$H NMR, 200 Mhz, analysis of the resulting urea derivative shows a doublet at 1.48 ppm, corresponding to 96% of the mixture and a doublet at 1.38 ppm accounting for 4% of the mixture.

A similar reaction was carried out with a sample of racemic 5-aminocarbonyl-5H-dibenzo[a,d]-cyclohepten-5, 10-imine. $^1$H NMR, 200 Mhz, analysis of the urea derivative from the racemic amine displayed a pair of methyl doublets of equal intensity at 1.38 ppm (J=6.8 Hz) and at 1.48 ppm (J=4.7 Hz).

4. Melting Point of 5% Racemic Mixture

Addition of 5% by weight of the 5S,10S enantiomer to pure 5R, 10R material provides a material having a melting point of 190°–236° C.

5. Optical Rotation and X-ray Crystallography

The optical rotation of the the enantiomer obtained from resolution with L-(+)-tartaric acid is −21.2°. The optical rotation of the the enantiomer obtained from resolution with D-(−)-tartaric acid is +22.6°.

Single crystal X-ray analysis of the enantiomer displaying a (+) rotation in the ORD indicates that the absolute configuration of the chiral centers at C-5 and C-10 is S. The absolute configuaration of the (−) enantiomer is therefore C-5 R and C-10 R.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude the specification.

What is claimed is:

1. A process for resolving a racemic mixture of 5-aminocarbonyl-5H-dibenzo[a,d]cycloheptene-5,10-imines into its component enantiomers comprising selectively crystallizing a first diasteriomeric tartrate salt from a mixture of two diasteriomeric tartrate salts of the 5-aminocarbonyl-5H-dibenzo[a,d]cycloheptene-5,10-imines in a mixture of ethanol and water, the 5-aminocarbonyl-5H-dibenzo[a,d]cycloheptene-5,10-imines having the formula

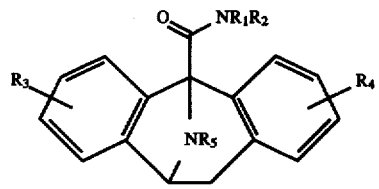

wherein wherein each of $R_1$ and $R_2$ is independently selected from hydrido, linear or branched alkyl groups of from one to twenty carbon atoms, alkenyl groups from two to twenty carbon atoms, alkynyl groups from two to twenty carbon atoms, cycloalkyl groups of three to eight carbon atoms, cycloalkenyl groups from three to eight carbon atoms, and wherein $R_1$ and $R_2$ may be taken together to form a N-containing cyclic structure having two to eight carbon atoms, any of the said groups being optionally substituted with one or more substituents selected from alkyl, haloalkyl, hydroxyalkyl, alkenyl, oxo, hydroxyl, alkoxy, thio, alkoxyalkyl, amino, halo, cyano or mercapto, and wherein $R_3$ and $R_4$ are independently selected from hydrido, linear or branched alkyl groups of from one to ten carbon atoms, alkenyl groups from two to ten carbon atoms, alkynyl groups from two to ten carbon atoms, hydroxyl, amino, alkylamino, alkoxy, cyano, nitro, haloalkyl and mercapto, and wherein $R_5$ is selected from hydrido, linear or branched alkyl groups of from one to about ten carbon atoms, alkenyl groups from two to ten carbon atoms, alkynyl groups from two to about ten carbon atoms, hydroxyl, phenyl, haloalkyl, aminoalkyl, 1-phenylmethyl, 2-phenylethyl and alkoxy, and wherein $R_1$ and $R_5$ taken together form a cyclic structure containing two nitrogen atoms possessing from two to six carbon atoms, any of the said groups being optionally substituted by alkyl, oxo, thio, alkoxy, hydroxy, amino, alkylamino, phenyl, haloalkyl and thio.

2. A process according to claim 1, wherein the mixture of salts is prepared using a single enantiomer of tartaric acid.

3. A process according to claim 2, wherein the volume ratio of ethanol to water in the ethanol and water mixture is from about 0.1:1 to about 10:1.

4. A process according to claim 3, wherein the volume ratio of ethanol to water in the ethanol and water mixture is about 1:1.

5. A process according to claim 4, wherein the tartaric acid is L-(+)-tartaric acid.

6. A process according to claim 4, wherein the tartaric acid is D-(−)-tartaric acid.

7. A process for resolving a racemic mixture of 5-aminocarbonyl-5H-dibenzo[a,d]cycloheptene-5,10-imines into its component enantiomers comprising (a) selectively crystallizing a first diasteriomeric tartrate salt from an ethanol and water solution of diasteriomeric tartrate salts of the 5-aminocarbonyl-5H-dibenzo [a,d]cycloheptene-5,10-imines, the mixture of diasteriomeric tartrate salts being prepared using a first enantiomer of tartaric acid;

(b) separating the first diasteriomeric tartrate salt from the solution and isolating a filtrate; and (c) forming a second diasteriomeric tartrate salt from material dissolved in the filtrate obtained in (b), the second diasteriomeric tartrate salt being prepared using a second enantiomer of tartaric acid:

the 5-aminocarbonyl-5H-dibenzo[a,d]cycloheptene-5,10-imines having the formula

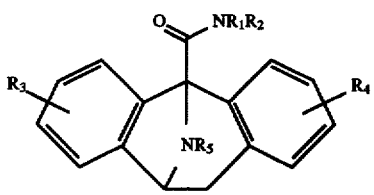

wherein each of $R_1$ and $R_2$ is independently selected from hydrido, linear or branched alkyl groups of from one to twenty carbon atoms, alkenyl groups from two to twenty carbon atoms, alkynyl groups from two to twenty carbon atoms, cycloalkyl groups of three to about eight carbon atoms, cycloalkenyl groups from three to eight carbon atoms, and wherein $R_1$ and $R_2$ may be taken together to form a N-containing cyclic structure having two to eight carbon atoms, any of the said groups being optionally substituted with one or more substituents selected from alkyl, haloalkyl, hydroxyalkyl, alkenyl, oxo, hydroxyl, alkoxy, thio, alkoxyalkyl, amino, halo, cyano or mercapto, and wherein $R_3$ and $R_4$ are independently selected from hydrido, linear or branched alkyl groups of from one to ten carbon atoms, alkenyl groups from two to ten carbon atoms, alkynyl groups from two to ten carbon atoms, hydroxyl, amino, alkylamino, alkoxy, cyano, nitro, haloalkyl and mercapto, and wherein $R_5$ is selected from hydrido, linear or branched alkyl groups of from one to ten carbon atoms, alkenyl groups from two to ten carbon atoms, alkynyl groups from two to ten carbon atoms, hydroxyl, phenyl, haloalkyl, aminoalkyl, 1-phenylmethyl, 2-phenylethyl and alkoxy, and wherein $R_1$ and $R_5$ taken together form a cyclic structure containing two nitrogen atoms possessing from two to six carbon atoms, any of the said groups being optionally substituted by alkyl, oxo, thio, alkoxy, hydroxy, amino, alkylamino, phenyl, haloalkyl and thio.

8. A process according to claim 7, wherein the first enantiomer of tartaric acid is L-(+)-tartaric acid.

9. A process according to claim 8, wherein the second enantiomer of tartaric acid is D-(−)-tartaric acid.

10. A process according to claim 9, wherein the volume ratio of ethanol to water in the solution is from about 0.1:1 to about 10:1.

11. A process according to claim 10, wherein the volume ratio of ethanol to water in the solution is about 1:1.

12. A process according to claim 11, further comprising (d), isolating the second diasteriomeric tartrate salt.

* * * * *